United States Patent
Tang et al.

(10) Patent No.: US 10,149,662 B2
(45) Date of Patent: Dec. 11, 2018

(54) 3D MECHANICAL PROBE

(75) Inventors: Shengli Tang, Shenzhen (CN); Leyun Bai, Shenzhen (CN); Zhenchang Wang, Shenzhen (CN); Zhenyu Chen, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 570 days.

(21) Appl. No.: 13/335,772

(22) Filed: Dec. 22, 2011

(65) Prior Publication Data

US 2012/0165678 A1 Jun. 28, 2012

(30) Foreign Application Priority Data

Dec. 27, 2010 (CN) .......................... 2010 1 0607330

(51) Int. Cl.
*A61B 8/00* (2006.01)
*A61B 8/08* (2006.01)

(52) U.S. Cl.
CPC .......... *A61B 8/4461* (2013.01); *A61B 8/4444* (2013.01); *A61B 8/483* (2013.01); *A61B 8/4281* (2013.01)

(58) Field of Classification Search
None
See application file for complete search history.

(56) References Cited

U.S. PATENT DOCUMENTS

| | | | | |
|---|---|---|---|---|
| 4,102,206 A | * | 7/1978 | Perdijon | .......................... 73/644 |
| 4,316,271 A | * | 2/1982 | Evert | ................... A61B 8/4281 |
| | | | | 600/445 |
| 4,517,840 A | * | 5/1985 | Thompson et al. | ............ 73/644 |
| 4,784,148 A | * | 11/1988 | Dow | ..................... G10K 11/355 |
| | | | | 600/446 |
| 4,807,634 A | * | 2/1989 | Enjoji | .................... G10K 11/02 |
| | | | | 600/437 |
| 5,049,130 A | * | 9/1991 | Powell | .......................... 600/467 |
| 5,088,495 A | * | 2/1992 | Miyagawa | ........... G10K 11/355 |
| | | | | 600/446 |
| 6,126,606 A | * | 10/2000 | Bergstoel | ...................... 600/459 |
| 2006/0100511 A1 | * | 5/2006 | Eriksen | ............... A61M 5/1408 |
| | | | | 600/431 |
| 2007/0016060 A1 | | 1/2007 | Hwang | |
| 2007/0293761 A1 | * | 12/2007 | Wickline | .................. A61B 8/12 |
| | | | | 600/459 |
| 2008/0161695 A1 | | 7/2008 | Kim et al. | |
| 2009/0049914 A1 | * | 2/2009 | Hasegawa | ....................... 73/584 |

FOREIGN PATENT DOCUMENTS

| | | |
|---|---|---|
| CN | 101354103 A | 1/2009 |
| CN | 101360459 A | 2/2009 |
| EP | 1878388 A1 | 1/2008 |

* cited by examiner

*Primary Examiner* — Bo Joseph Peng
(74) *Attorney, Agent, or Firm* — Polsinelli LLP; Kory D. Christensen

(57) ABSTRACT

A three-dimensional (3D) mechanical probe for ultrasonic imagining is disclosed.

8 Claims, 8 Drawing Sheets

3D MECHANICAL PROBE

CROSS-REFERENCE TO RELATED APPLICATIONS

This application claims the benefit of Chinese Patent Application No. 201010607330.9, filed on Dec. 27, 2010, which is incorporated herein by reference in its entirety.

TECHNICAL FIELD

The present disclosure relates to ultrasonic probes.

SUMMARY OF THE INVENTION

Disclosed herein are embodiments of a three-dimensional (3D) mechanical probe for diagnostic ultrasound and a volume compensation structure in a 3D mechanical probe.

DETAILED DESCRIPTION

A 3D mechanical probe for use in diagnostic ultrasound typically includes a stepping motor to serve as a drive power source. The stepping motor drives a sound head to swing within a certain angular range through a drive system under signal control. Like a conventional probe, the 3D mechanical probe can transmit an ultrasonic wave and receive an echo wave carrying human tissue information at each swinging angle, so as to image human tissue at each angle within the swinging range without the need for sliding or swinging the probe on the surface of a human body.

Figure 1:
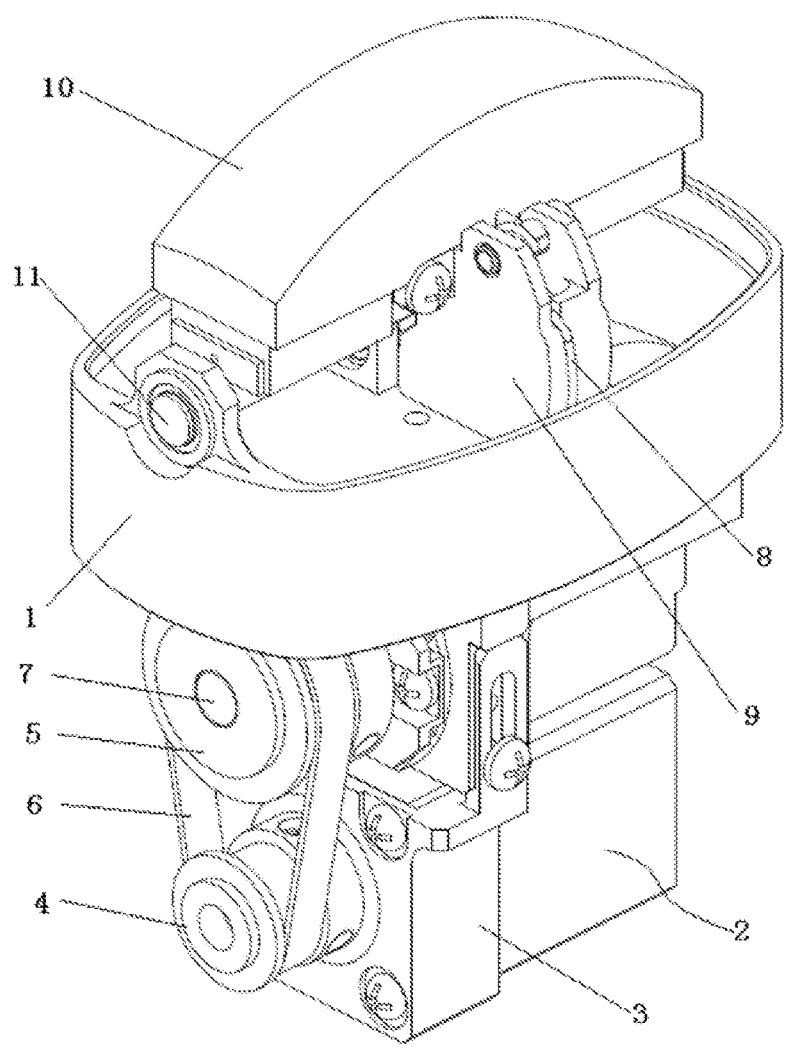
FIG. 1 is a perspective view of an internal structure of a conventional 3D mechanical probe.

FIG. 1 is a perspective view of an internal structure of a conventional 3D mechanical probe. A motor 2 is fixed on a base 1 through a motor stand 3. A driving synchronous pulley 4 is fixedly connected to an output shaft of the motor 2. The driving synchronous pulley 4 transmits an output motion of the motor 2 to a driven synchronous pulley 5 through a synchronous belt 6. The driven synchronous pulley 5 is fixedly connected to a driving shaft 7. The driving shaft 7 is supported on the base 1 and is capable of free rotation. A driven wheel 9 is supported on the base 1 through a rotating shaft 11 and may rotate about the rotating shaft 11. A sound head 10 is fixedly connected to the driven wheel 9. The driving shaft 7 drives the driven wheel 9 to swing through a rope 8, and the sound head 10, which is fixedly connected to the driven wheel 9, swings accordingly.

Figure 2:
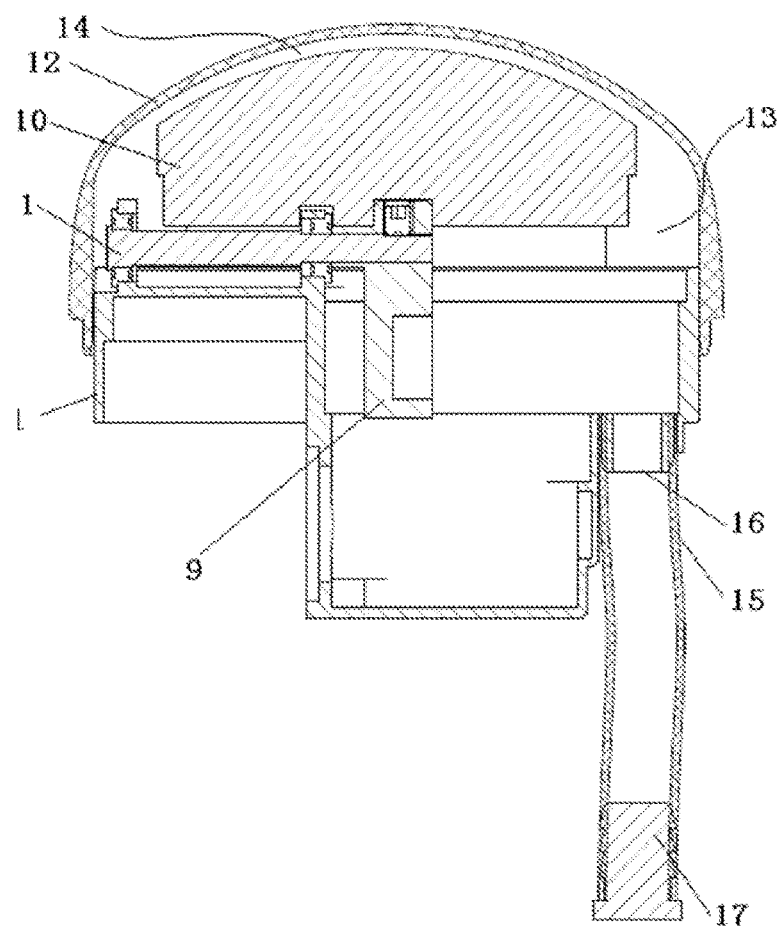
FIG. 2 is a schematic view of the conventional 3D mechanical probe.

As shown in FIG. 2, the base 1 is connected to an acoustic window 12, an airtight space 13 is provided between the base 1 and the acoustic window 12, and the airtight space 13 is surrounded by the base 1, the acoustic window 12, and other connecting structures (e.g., the driving shaft 7 and the like, not shown). The sound head 10 swings in the airtight space 13. The airtight space 13 is filled with a coupling liquid, which fills a gap 14 between the sound head and the acoustic window to conduct an ultrasonic wave.

During normal operation, the 3D mechanical probe generally operates within a certain temperature range. When an operating temperature of the 3D mechanical probe rises, the volume of the coupling liquid in the airtight space 13 expands, producing a large pressure on the acoustic window 12 and the base 1. The pressure may affect the sealed connection between the acoustic window 12 and the base 1. When the pressure is too high, the sealed connection between the acoustic window 12 and the base 1 may fail, causing leakage of the coupling liquid.

In order to reduce the effect of the internal pressure of the airtight space on the acoustic window 12 and the base 1, as well as the sealed connection therebetween, a volume compensation structure is usually disposed to compensate for the volume change of the coupling liquid. When the coupling liquid expands, the volume compensation structure accommodates a part of the coupling liquid, lowers the internal pressure of the airtight space, and reduces the effect on the acoustic window, the base, and the connection surface therebetween. Generally, a hose 15 in communication with the airtight space 13 is connected to the base 1, and the volume change of the hose 15 is utilized to buffer the effect of the pressure.

Figure 3A:
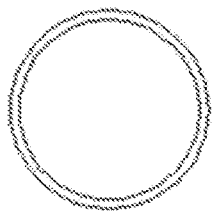
FIGS. 3a to 3d are schematic views showing forces applied on a hose and stretching of a wall of the hose of the conventional 3D mechanical probe.

Conventionally, the hose has a circular section. After oil-injection (i.e., the coupling liquid is injected into the airtight space) and plug-up (i.e., an end of the hose is sealed using a plug head or other method) at a normal temperature, the section of the hose is still circular, and the pressures inside and outside the hose are the same, as shown in FIG. 3a. When the temperature rises, the volume of the coupling liquid expands, and the pressure of the coupling liquid produced on the interior of the hose increases, so that the sectional radius of the hose is increased, and the hose has a larger capacity to accommodate the increased coupling liquid in the airtight space due to a temperature rise. The sectional radius of the hose is increased, the perimeter of the section of the hose is also increased, and the wall of the hose is stretched.

Figure 3B:
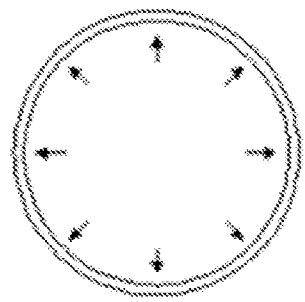
Figure 3C:
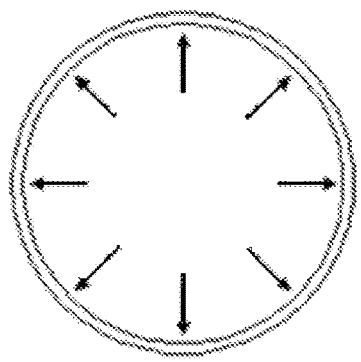
Figure 3D:
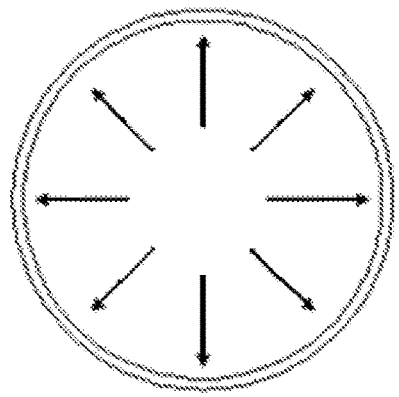

Since the force for stretching the wall of the hose comes from the pressure of the coupling liquid in the hose, and only a large internal pressure can stretch the wall of the hose, the pressure of the internal coupling liquid is high. At this time, the pressure inside the hose is higher than the external pressure, as shown in FIG. 3b. The more the volume of the coupling liquid changes, the larger the sectional area of the hose is, the larger the perimeter of the section of the hose is, the more the wall of the hose is stretched, and the larger the pressure inside the hose is, as shown in FIGS. 3b to 3d. The probe must bear a high internal pressure at sealed locations (e.g., the location of the sealed connection between the acoustic window and the base), which often causes a failure of the sealed connection and leakage of the coupling liquid.

Accordingly, the use of a hose with a circular section requires strong sealing structures and connecting structures. In addition, to reduce the internal pressure of the hose in the expanded state, the elastic modulus of the hose must be sufficiently small, and the wall of the hose must be as thin as possible, which requires a more expensive hose material and manufacturing process.

In addition, when the operating temperature of the 3D mechanical probe is lowered, the volume of the coupling liquid shrinks, and the area surrounded by the sectional inner contour of the hose decreases. As used herein, "section" refers to a cross section perpendicular to an axis of the hose. When the temperature is lowered under a temperature that maintains a balance of internal and external pressures in the hose (i.e., the temperature corresponding to FIG. 3a), the internal pressure of the hose is lower than the external pressure. As a result, a negative pressure is formed inside the hose. In this case, external air enters the airtight space 13 from positions with poor sealing such as the end of the hose where it is plugged and the location where the hose is connected to the base. If the airtightness of the material is poor, the external air will enter the hose from the wall of the hose. Once the air enters the hose, bubbles may be formed in the coupling liquid and may move to area gap 14 between the sound head and the acoustic window. Since the bubbles are strong reflectors of the ultrasonic wave, the presence of bubbles in the coupling liquid severely affects the ultrasonic imaging quality.

The present disclosure is directed to a 3D mechanical probe capable of providing effective compensation for volume changes of a coupling liquid within an operating temperature range of a hose, in which the coupling liquid has a low internal pressure on an acoustic window, a base, and a sealed connection structure therebetween, such that the sealed connection does not fail easily.

Figure 4:
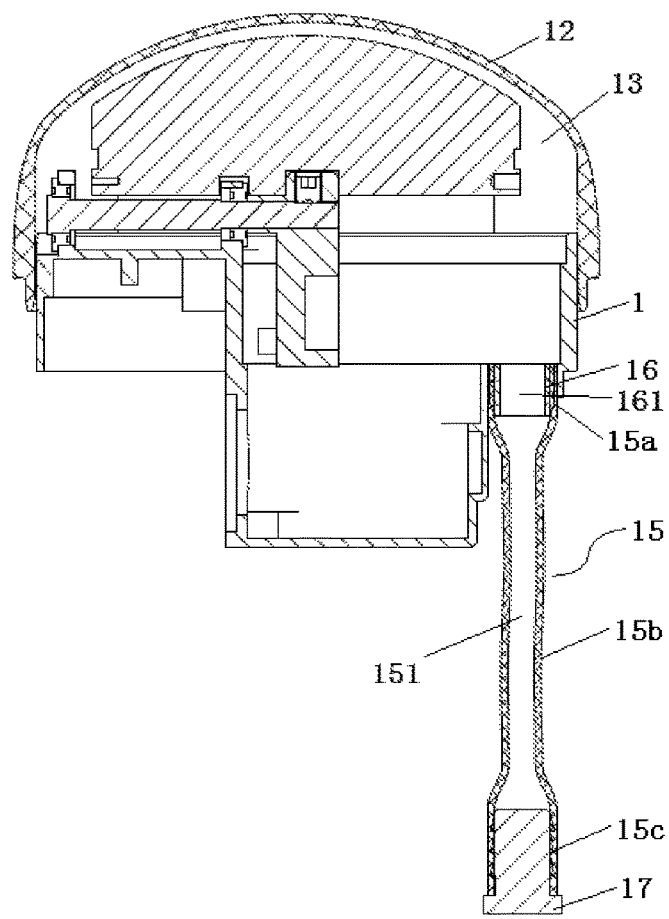
FIG. 4 is a schematic view of a 3D mechanical probe according to an embodiment of the present disclosure.

As shown in FIG. 4, a 3D mechanical probe according to one embodiment of the present disclosure includes a base 1, an acoustic window 12, a hose 15, and a plug head 17. An airtight space 13 is provided between the base 1 and the acoustic window 12. The airtight space 13 is surrounded by the base 1, the acoustic window 12, and other connecting structures (for example, a driving shaft 7, not shown). The base 1 is connected to a connector 16. The connector 16 includes a channel 161 passing through the connector 16 and in communication with the airtight space 13. The hose 15 includes a head 15a, a middle 15b, and a tail 15c. The head 15a of the hose 15 is connected to the connector 16. A cavity 151 of the hose 15 is in communication with the airtight space 13 through the channel 161 of the connector 16. The tail 15c of the hose 15 is connected to the plug head 17 through which the cavity 151 of the hose 15 is closed.

As shown in FIGS. 5 to 8, different from a conventional hose having an overall circular section, in the hose 15 according to this embodiment, sectional inner contours of the head 15a and the tail 15c are circular, while a sectional inner contour of the middle 15b is non-circular; that is, the sectional inner contour of the middle 15b satisfies the condition that, among radii of curvature at points on the sectional inner contour, radii of curvature at at least one portion of the points are greater than radii of curvature at at least one other portion of the points. Persons skilled in the art know that radii of curvature at all points on a circular contour are equal. However, in one embodiment, the shape of an inner contour of a section perpendicular to an axis at every place in at least one part of the length of the hose is a non-circular shape; that is, radii of curvature at at least one part of points on the sectional inner contour are unequal, and radii of curvature at at least one part of points are greater than radii of curvature at at least the other part of points.

As used herein, "sectional inner contour" refers to a contour of a cavity surrounded by an inner side on a cross section perpendicular to an axis of the hose, and "sectional outer contour" refers to a contour of an outer side on the cross section.

In one embodiment, perimeters of the sectional inner contours of the head 15a and the tail 15c of the hose are smaller than a perimeter of the sectional inner contour of the middle 15b. In this way, the connector 16 and the plug head 17 connected to the head 15a and the tail 15c of the hose can be made relatively small to save space, while the perimeter of the sectional inner contour of the middle 15b can be made relatively large, so as to realize a large volume change range, thereby increasing the compensable volume range.

In other embodiments, the sectional inner contour and sectional outer contour of the head 15a and the tail 15c may be in any other shape, as long as the purpose of sealing and connection is achieved. The sectional inner contour of the middle 15b is non-circular, and the sectional outer contour of the middle 15b may also be in any other shape.

Figure 5:
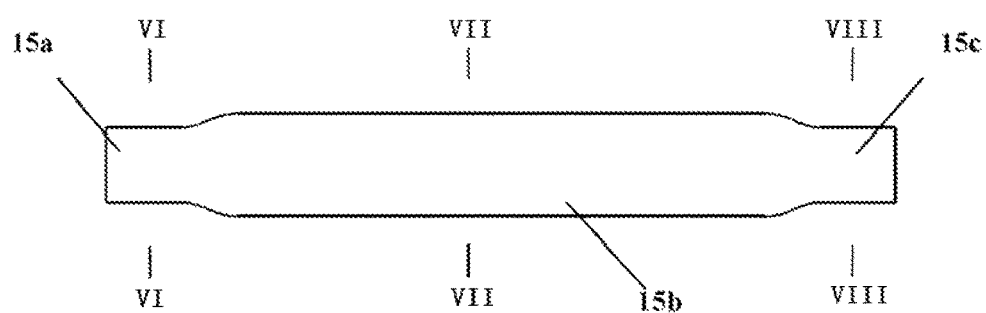
FIG. 5 is a schematic view showing a hose according to an embodiment of the present disclosure.
Figure 6:
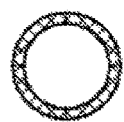
FIG. 6 is a schematic cross section view of the hose along the line I-I in FIG. 5.
Figure 7:
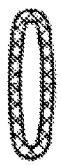
FIG. 7 is a schematic cross section view of the hose along the line II-II in FIG. 5.
Figure 8:
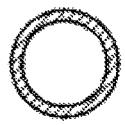
FIG. 8 is a schematic cross section view of the hose along the line III-III in FIG. 5.
Figure 9:
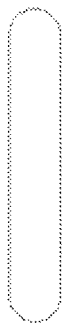
FIG. 9 is a schematic view showing a section of a hose according to an embodiment of the present disclosure.
Figure 10:
FIG. 10 is a schematic view showing a section of a hose according to an embodiment of the present disclosure.

In the embodiment of FIG. 5, the sectional inner contour of the middle 15b of the hose is non-circular. In one embodiment, the sectional inner contour may be elliptical. In other embodiments, the sectional inner contour of the middle 15b of the hose may also be other shapes, as shown in FIGS. 9 to 10. Herein, the shape in FIG. 9 and the like are referred to as a "long circle," and the shape in FIG. 10 and the like are referred to as a "double curved shape." The shape of the sectional inner contour of the middle 15b of the hose is not limited to the ellipse, long circle, and double curved shape shown in FIGS. 9 to 10, and may also be any other non-circular shapes, as long as the area surrounded by the inner contour can be increased through deformation of the inner contour without stretching the wall of the hose.

In one embodiment, the middle 15b of the hose may have a cross section of equal wall thickness, so that the volume of the hose can be reduced to save space, a small force is required for changing the section of the hose, forces applied on the hose are relatively even, and it is easy to inspect incoming materials in the production process. In other embodiments, the middle 15b of the hose may also have a cross section of unequal wall thickness. The head 15a and the tail 15c of the hose may also have cross sections of equal wall thickness, which may be small to reduce the structural space as much as possible. However, for purposes of connection and sealing, the wall thickness of the head 15a and the tail 15c may also be made large, so as to have cross sections of unequal wall thickness.

Figure 11:
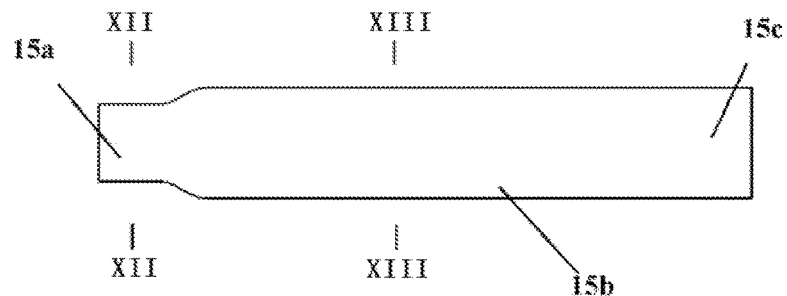
FIG. 11 is a schematic view showing a hose according to an embodiment of the present disclosure.
Figure 12:
FIG. 12 is a schematic cross section view of the hose along the line IV-IV in FIG. 11.
Figure 13:
FIG. 13 is a schematic cross section view of the hose along the line V-V in FIG. 11.

In the embodiment of FIG. 5, the perimeters of the sectional inner contours of the head 15a and the tail 15c of the hose 15 are smaller than the perimeter of the sectional inner contour of the middle 15b. In other embodiments, either or both of the head 15a and the tail 15c may be made to have the same perimeter of the sectional inner contour as that of the middle 15b. For example, as shown in FIGS. 11 to 13, the perimeter of the sectional inner contour of the head 15a of the hose is smaller than the perimeters of the sectional inner contours of the middle 15b and the tail 15c, and the perimeters of the sectional inner contours of the middle 15b and the tail 15c are the same. On one hand, the size of the connector 16 connected to the head 15a of the hose may be reduced, which usually has a small space, thereby limiting the size of the hose. On the other hand, one end is large, and the other end is small in the inner side of the hose (the inner sides of the middle 15b and the tail 15c of the hose are large, and the inner side of the head 15a of the hose is small), so that the core can be easily drawn out of the tail 15c of the hose without damaging the wall of the hose in the fabrication of the hose, thereby ensuring the quality of the hose.

In other embodiments, the perimeters of the sectional inner contours of the head 15a and the tail 15c of the hose 15 may also be greater than the perimeter of the sectional inner contour of the middle 15b.

Figure 14:
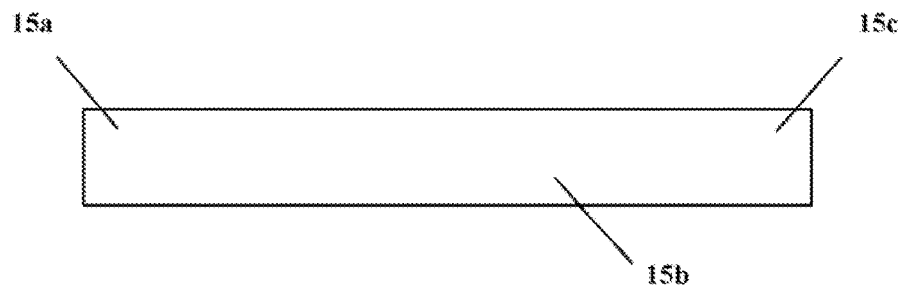
FIG. 14 is a schematic view showing a hose according to an embodiment of the present disclosure.
Figure 15:
FIG. 15 is a schematic side view of the hose in FIG. 14.

Further, as shown in FIGS. 14 and 15, in other embodiments, the sectional inner contours of the head 15a, the middle 15b, and the tail 15c of the hose may also have the same size, allowing the hose to be made long and simplifying the manufacturing process.

In the above embodiments, for the hose with the middle 15b having a non-circular sectional inner contour, an area surrounded by the sectional inner contour in a natural state is herein referred to as S1, an area surrounded by the sectional inner contour in an operating state is herein referred to as S2, and an area surrounded by the sectional inner contour when the sectional inner contour changes to a circle and the perimeter thereof remains unchanged is herein referred to as S3. In some embodiments, S1 and S2 may always satisfy S1<S2, when operated such that an internal pressure of the hose is constantly greater than an external pressure in the operating state. Alternatively, S2 and S3 always satisfy S2<S3, thereby ensuring that the internal pressure of the hose in the operating state is constantly smaller than a pressure deforming the wall of the hose to a circle, so that the wall of the hose is not stretched, such that the internal pressure of the hose is small. In one embodiment, S1<S2<S3 may also be satisfied. Herein, the "operating state" of the hose refers to a state in which the hose of the probe is in an operating temperature; the "natural state" refers to a state in which the hose is in a natural state when a coupling liquid is not injected before assembly of the probe, and the area surrounded by the sectional inner contour refers to an area of the cavity surrounded by the inner contour of the section, as described in detail below.

For a closed shape with a certain perimeter, when the shape is a circle, the area is the largest; when the shape is a non-circular shape, the area depends on the specific shape, in which a minimum approaches 0, a maximum approaches the area of the circle. The area changes from the minimum to the maximum, while the perimeter remains unchanged, so that the area can be changed by only changing the shape.

Figure 16A:
FIGS. 16a to 16d are schematic views showing of forces applied on a hose and deformation of the hose according to an embodiment of the present disclosure.
Figure 16B:
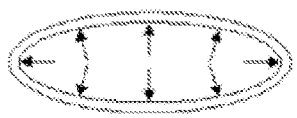
Figure 16C:
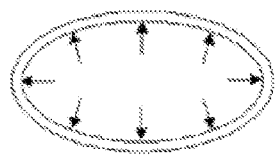
Figure 16D:
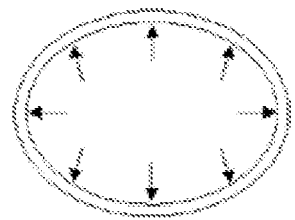

In one embodiment, a hose with a non-circular sectional inner contour is used to perform volume compensation on the coupling liquid in the airtight space 13 of the probe. Use of the non-circular sectional inner contour facilitates deformation, the changes of the area surrounded by the sectional inner contour are known, and the perimeter of the sectional inner contour remains unchanged when the area surrounded by the sectional inner contour is changed. The sectional inner contour of the hose in the natural state, i.e., when the internal and external pressures are the same, is non-circular, as shown in FIG. 16a. When the internal pressure of the hose is greater than the external pressure, the area surrounded by the sectional inner contour of the hose is increased, as shown in FIGS. 16b to 16d.

The increase of the area surrounded by the sectional inner contour of the hose is achieved by deforming the sectional inner contour of the hose without increasing the perimeter, i.e., without stretching the wall of the hose, so the deformation is quite easy. Since no force for stretching the wall of the hose is required, the pressure inside the hose may be small (the force stretching the wall of the hose is provided by the pressure of the coupling liquid in the hose). The larger the difference between the internal pressure of the hose and the external pressure, the larger the area surrounded by the sectional inner contour of the hose is. The area surrounded by the sectional inner contour of the hose may be positively correlated with the internal pressure of the hose. Therefore, the area S1 surrounded by the sectional inner contour of the hose in the natural state, the area S2 surrounded by the sectional inner contour of the hose in the operating state, and the area S3 surrounded by the sectional inner contour of the hose when the sectional inner contour changes to a circle and the perimeter thereof remains unchanged may be made to satisfy the condition that S2 is constantly greater than S1 and/or S2 is constantly smaller than S3. Since S2 is constantly greater than S1, the internal pressure of the hose is constantly greater than the external pressure in the operating state, thereby preventing external air from entering the airtight space. Since S2 is constantly smaller than S3, the hose keeps operating in the state of a non-circular sectional inner contour, so that the wall of the hose is not stretched, and the pressure in the airtight space is small.

After the hose is connected to the base, injected with oil, and plugged, only the volume of the coupling liquid in the airtight space of the probe is changed due to the influence of temperature. Therefore, when the hose is mounted, the coupling liquid is injected, and the hose is plugged, the initial pressure of the coupling liquid in the airtight space and the hose is properly adjusted (i.e., the initial S2 is adjusted), so that S2 is still greater than S1 when the hose is at the lowest operating temperature, the coupling liquid has a minimum volume, and the minimum S2 is reached. S2 is still smaller than S3 when the hose is at the highest operating temperature, the coupling liquid has the maximum volume, and the maximum S2 is reached. In this way, S2 is constantly greater than S1 and constantly smaller than S3 in the operating state.

When the hose 15 is in the natural state, the internal pressure and the external pressure are the same, as shown in FIG. 16a. When oil is injected and the hose is plugged at a normal temperature, the hose swells a little, as shown in FIG. 16c. At the highest operating temperature of the hose, the hose expands to the maximum, but the sectional inner contour is still non-circular, as shown in FIG. 16d. At the lowest operating temperature of the hose, the hose shrinks to the minimum, but the area surrounded by the sectional inner contour is still greater than the area in the natural state, as shown in FIG. 16b. In this way, in the operating temperature range of the hose, the hose is always in an expanded state, and the internal pressure is constantly greater than the external pressure, so as to prevent external air from entering the airtight space 13. When the temperature changes, the volume change of the hose 15 is achieved through deformation of the section without stretching the wall of the hose. For a hose that has not reached the state of circular sectional inner contour, such a change requires a small force and produces a small pressure on the internal coupling liquid, and thus has a small effect on the sealing structure and a connecting structure of the acoustic window and the base of the probe, so as to avoid the problem that a large pressure of the internal coupling liquid causes a failure of the sealing structure between the acoustic window and the base.

In one embodiment, the sectional inner contour of the hose deforms according to temperature changes in the operating temperature range to compensate for the volume changes of the coupling liquid in the airtight space. The hose keeps operating in the state of a non-circular sectional inner contour, and the volume changes of the coupling liquid caused by the operating temperature changes can be compensated for without stretching the wall of the hose, so as to reduce the pressure in the airtight space. This reduces the requirement for high performance indices, such as airtightness and elastic modulus. The deformation of the hose is mainly realized through the deformation of the sectional inner contour of the hose without stretching the wall of the hose, thus having no strict requirement for the wall thickness. The airtight space does not produce a large internal pressure, increasing the reliability of each connecting structure and reducing cost. Also, the pressure of the internal coupling liquid is always slightly greater than the external pressure, thereby preventing external air from entering the internal airtight space to impair the imaging quality.

The invention is described above through specific embodiments, but the invention is not limited to these embodiments. Various modifications, equivalent replacements, and variations can be made without departing from the spirit and scope of the invention.

What is claimed is:

1. A three-dimensional (3D) mechanical probe, comprising:
    a base,
    an acoustic window,
    a hose that has an open, connection end, a closed end, and a central portion between the open and closed ends, and
    a plug head,
    wherein
    the acoustic window is connected to the base,
    a sealed space is provided between the acoustic window and the base,
    the base is connected to a connector,
    the open, connection end of the hose is connected to the connector,
    the connector comprises a channel passing through the connector,
    the central portion of the hose is in communication with the sealed space through the channel,
    the plug head is connected to and seals the closed end of the hose,
    the sealed space and the hose are filled with a coupling liquid,
    wherein:
        the central portion of the hose has a cross-sectional inner circumference, and, in a natural, uncompressed state, a natural, non-circular, inner cross-section taken perpendicular to a lengthwise-extending, central axis of the central portion;
        in a state of minimum operating pressure of the coupling liquid, the central portion is open, permitting flow of the liquid from the sealed space into the central portion;
        in a state of maximum operating pressure of the coupling liquid, the central portion retains an expanded, non-circular, inner cross-section;
        the cross-sectional inner circumference of the central portion remains constant while the shape and cross-sectional area of the central portion vary from the state of minimum operating pressure to the state of maximum operating pressure,
        whereby the volume of the coupling liquid in the central portion increases as the temperature of the coupling liquid increases and decreases as the temperature of the coupling liquid decreases.

2. The 3D mechanical probe according to claim 1, wherein the cross-sectional inner circumference of the central portion is in the shape of an ellipse, a long circle, or a double curved shape.

3. The 3D mechanical probe according to claim 1, wherein the state of minimum operating pressure corresponds to a lowest operating temperature and the state of maximum operating pressure correspond to a highest operating temperature.

4. The 3D mechanical probe according to claim 1, wherein the open end and closed end have an inner cross-section taken perpendicular to the central axis that is different from the central portion.

5. The 3D mechanical probe according to claim 4, wherein the inner cross-section of the open end and closed end are circular.

6. The 3D mechanical probe according to claim 4, wherein the open end and closed end have a thickness that is different from a thickness of the central portion.

7. The 3D mechanical probe according to claim 1, wherein a perimeter of a sectional inner contour of the open, connection end is smaller than a perimeter of a sectional inner contour of the central portion and a perimeter of a sectional inner contour of the closed end.

8. The 3D mechanical probe according to claim 1, wherein the coupling liquid is filled through the closed end of the hose and the plug head is installed in the closed end after the coupling liquid reaches the closed end.

* * * * *